United States Patent
Doi et al.

(10) Patent No.: US 9,169,176 B2
(45) Date of Patent: Oct. 27, 2015

(54) PYRENE COMPOUND AND ORGANIC ELECTROLUMINESCENT DEVICE INCLUDING THE SAME

(75) Inventors: Noriyuki Doi, Numazu (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 420 days.

(21) Appl. No.: 13/395,635

(22) PCT Filed: Jul. 14, 2010

(86) PCT No.: PCT/JP2010/004577
§ 371 (c)(1),
(2), (4) Date: Mar. 12, 2012

(87) PCT Pub. No.: WO2011/030493
PCT Pub. Date: Mar. 17, 2011

(65) Prior Publication Data
US 2012/0168736 A1    Jul. 5, 2012

(30) Foreign Application Priority Data
Sep. 14, 2009  (JP) .................................. 2009-211977

(51) Int. Cl.
   H01L 51/54    (2006.01)
   C07C 15/20    (2006.01)
   C07C 15/38    (2006.01)
   C09K 11/06    (2006.01)
   H05B 33/14    (2006.01)
   H01L 51/00    (2006.01)

(52) U.S. Cl.
   CPC .................. C07C 15/38 (2013.01); C09K 11/06 (2013.01); H01L 51/0058 (2013.01);
   (Continued)

(58) Field of Classification Search
   CPC .... C07C 15/38; C07C 2103/50; C09K 11/06; C09K 2211/1011; H01L 2251/308; H01L 51/0054; H01L 51/0055; H01L 51/0058; H01L 51/006; H05B 33/14
   See application file for complete search history.

(56) References Cited

U.S. PATENT DOCUMENTS

2004/0137270 A1*  7/2004  Seo et al. ................. 428/690
2004/0209118 A1* 10/2004  Seo et al. ................. 428/690
(Continued)

FOREIGN PATENT DOCUMENTS

JP      6-219973 A      8/1994
JP      2007-191603 A   8/2007
(Continued)

*Primary Examiner* — Dawn Garrett
(74) *Attorney, Agent, or Firm* — Canon U.S.A. Inc., IP Division

(57) ABSTRACT

A pyrene compound represented by general formula (1): wherein X represents one of a naphthalene ring and phenanthrene ring: when X represents the naphthalene ring, a 1-pyrenyl group indicated in general formula (1) is bonded to a 2-position of the naphthalene ring; when X represents the phenanthrene ring, the 1-pyrenyl group is bonded to one of a 2-position and a 3-position of the phenanthrene ring; and R1 and R2 are each independently selected from a hydrogen atom and an alkyl group.

[Chem. 1]

General formula (1)

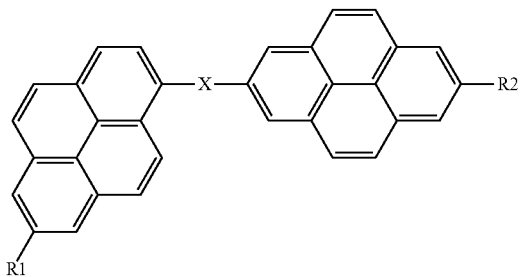

13 Claims, 1 Drawing Sheet

(52) U.S. Cl.
  CPC ........... *H05B 33/14* (2013.01); *C07C 2103/50* (2013.01); *C09K 2211/1011* (2013.01); *H01L 51/006* (2013.01); *H01L 51/0054* (2013.01); *H01L 51/0055* (2013.01); *H01L 2251/308* (2013.01)

(56) References Cited

U.S. PATENT DOCUMENTS

| 2005/0174044 | A1* | 8/2005 | Miura | 313/504 |
| 2006/0154107 | A1* | 7/2006 | Kubota et al. | 428/690 |
| 2008/0012475 | A1* | 1/2008 | Oyamada et al. | 313/504 |
| 2008/0224603 | A1* | 9/2008 | Hashimoto et al. | 313/504 |
| 2008/0268285 | A1* | 10/2008 | Okinaka et al. | 428/691 |
| 2008/0290794 | A1* | 11/2008 | Yuasa | 313/504 |
| 2009/0278447 | A1* | 11/2009 | Saitoh et al. | 313/504 |

FOREIGN PATENT DOCUMENTS

| JP | 2007-227152 | * | 9/2007 |
| JP | 2008-255099 | A | 10/2008 |
| JP | 2009-221442 | A | 10/2009 |
| JP | 2010-123917 | A | 6/2010 |
| KR | 1020090016035 | A | 2/2009 |
| WO | 2006/057325 | A1 | 6/2006 |

* cited by examiner

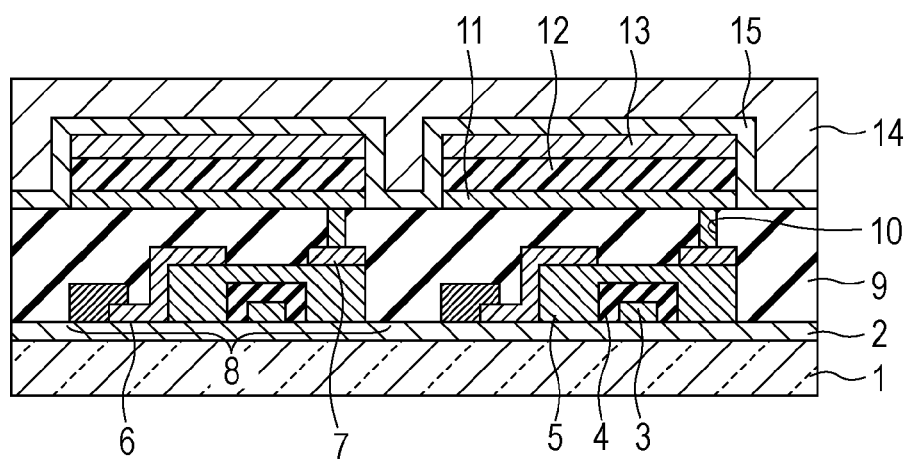

PYRENE COMPOUND AND ORGANIC ELECTROLUMINESCENT DEVICE INCLUDING THE SAME

TECHNICAL FIELD

The present invention relates to a novel pyrene compound and an organic electroluminescent (EL) device including the novel pyrene compound.

BACKGROUND ART

An organic EL device is a device that includes an anode, a cathode, and an organic compound layer interposed between the anode and the cathode. Holes and electrons supplied from the anode and the cathode excite the zorganic compound contained in the organic compound layer and light is emitted when the organic compound returns to its ground state.

In PTL 1, a compound A1 represented as below is used as a host material of an emission layer of a blue light-emitting device.

[Chem. 1]

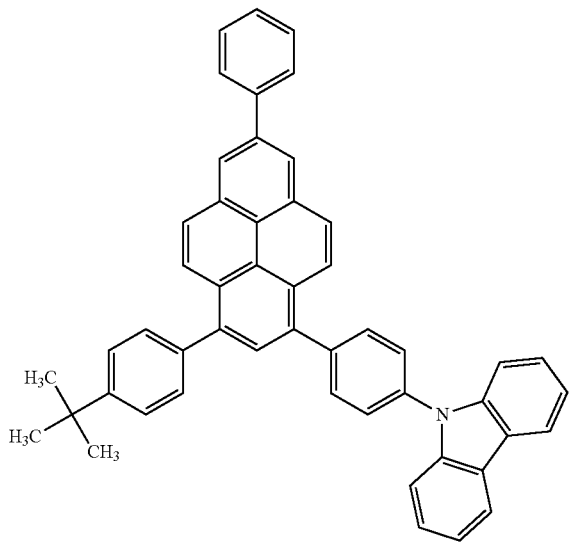

A1

CITATION LIST

Patent Literature

PTL 1: Japanese Patent Laid-Open No. 2007-191603 (no corresponding foreign application)

SUMMARY OF INVENTION

A material having a wide band gap is used as a host material of a blue emission layer. Such a material tends to have a deep highest-occupied molecular orbital (HOMO) level due to the wide band gap. Since the HOMO level is deep, the barrier between HOMO levels becomes wider between the blue emission layer and a hole transport layer adjacent to the blue emission layer. This shortens the luminance half life of the organic EL device.

PTL 1 describes an organic EL device that includes the compound A1 as the host material of a blue emission layer. The luminance half life of the organic EL device is only about 4,000 hours when continuously driven at a current density of 10 mA/cm$^2$.

The present invention provides a novel organic compound that has a shallow HOMO level. The present invention also provides an organic EL device that contains the novel organic compound and has a long luminance half life.

An aspect of the present invention provides a pyrene compound represented by general formula (1) below:

[Chem. 2]

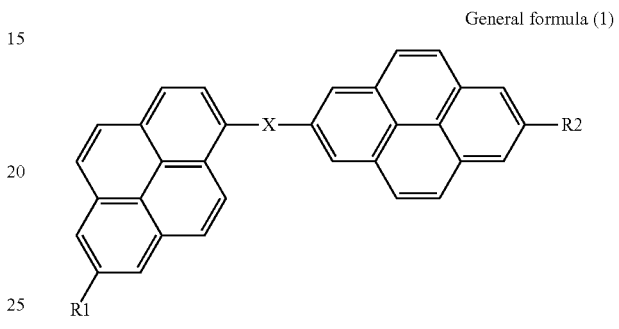

General formula (1)

In general formula (1), X represents one of a naphthalene ring and a phenanthrene ring. When X represents a naphthalene ring, a 1-pyrenyl group indicated in general formula (1) is bonded to the 2-position of the naphthalene ring. When X represents a phenanthrene ring, the 1-pyrenyl group is bonded to the 2- or 3-position of the phenanthrene ring. R1 and R2 are each independently selected from a hydrogen atom and an alkyl group.

According to this aspect of the invention, a pyrene compound having a wide band gap and a shallow HOMO level can be provided. An organic EL device that contains this pyrene compound has a long luminance half life.

BRIEF DESCRIPTION OF DRAWINGS

FIG. 1 is a schematic cross-sectional view showing an organic EL device and a thin film transistor (TFT) device connected to the organic EL device.

DESCRIPTION OF EMBODIMENTS

A novel pyrene compound according to an embodiment of the present invention is represented by general formula (1) below.

[Chem. 3]

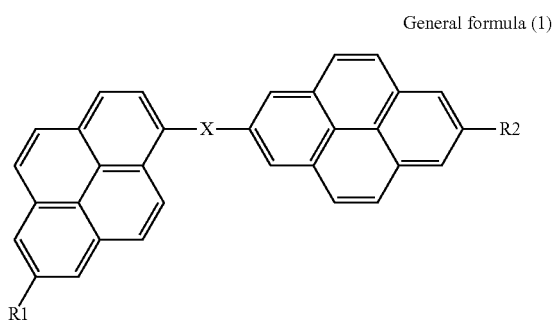

General formula (1)

In general formula (1), X represents one of a naphthalene ring and a phenanthrene ring. When X represents a naphthalene ring, a 1-pyrenyl group indicated in general formula (1) is bonded to the 2-position of the naphthalene ring. When X represents a phenanthrene ring, the 1-pyrenyl group is bonded to the 2- or 3-position of the phenanthrene ring. X may contain a substituent. R1 and R2 are each independently selected from a hydrogen atom and an alkyl group.

This pyrene compound, i.e., a compound that includes a 1-pyrenyl group on the left side of general formula (1) and X bonded to the 1-pyrenyl group, has a wide band gap and a shallow HOMO level. According to a molecular orbital calculation, the HOMO level of the pyrene compound is localized on the 1-pyrenyl group and the naphthalene or phenanthrene ring. The band gap of the molecule is determined by the 1-pyrenyl group and the naphthalene or phenanthrene ring bonded to the 1-pyrenyl group. The 2-pyrenyl group indicated on the right side of general formula (1) renders the HOMO level shallower without substantially changing the value of the band gap determined by the 1-pyrenyl group and the naphthalene or phenanthrene ring bonded to the 1-pyrenyl group. Note that the "shallow HOMO level" means that the vacuum level is close to the HOMO level.

The substituents represented by R1 and R2 in general formula (1) are each independently selected from a hydrogen atom and an alkyl group. Specific examples of the alkyl group include chain alkyl groups such as a methyl group, an ethyl group, an isopropyl group, a n-butyl group, a sec-butyl group, a tert-butyl group, a pentyl group, a hexyl group, an octyl group, a decyl group, a dodecyl group, a tridecyl group, a tetradecyl group, a pentadecyl group, a hexadecyl group, and an octadecyl group; and cyclic alkyl groups such as a cyclopentyl group and a cyclohexyl group. Among these, a tert-butyl group is suitable. R1 and R2 are added to the main backbone.

The reason for using the tert-butyl group is at least one of the following two.

First, the tert-butyl group improves the hole injectability. Second, the tert-butyl group is bulky and can thus suppress association of the pyrene compound.

When X in general formula (1) represents a naphthalene ring, the 1-pyrenyl group may be bonded to the 2-position of the naphthalene ring. When X represents a phenanthrene ring, the 1-pyrenyl group may be bonded to the 2- or 3-position of the phenanthrene ring.

This is because the dihedral angle formed between the naphthalene or phenanthrene ring and the 1-pyrenyl group is small. In other words, the intramolecular twist is little and the molecular conjugation between two planes remains unbroken.

The position at which the 2-pyrenyl group is bonded to the naphthalene or phenanthrene ring is not particularly limited. In particular, when X represents a naphthalene ring, the 6-position of the naphthalene ring may be bonded to the 2-pyrenyl group. In a phenanthrene ring having the 2-position bonded to the 1-pyrenyl group, one of the 6- and 7-positions of the phenanthrene ring may be bonded to the 2-pyrenyl group. In particular, the 7-position of the phenanthrene ring may be bonded to the 2-pyrenyl group. In a phenanthrene ring having the 3-position bonded to the 1-pyrenyl group, one of the 6- and 7-positions of the phenanthrene ring may be bonded to the 2-pyrenyl group. In particular, the 7-position of the phenanthrene ring may be bonded to the 2-pyrenyl group.

The calculation results of the HOMO level of a compound A2 represented as below, which is an example of the pyrene compound of the present invention, and a compound A3 represented as below, which is a comparative example, are described below. The HOMO level was calculated by a molecular orbital method on the basis of the Austin Model 1.

[Chem. 4]

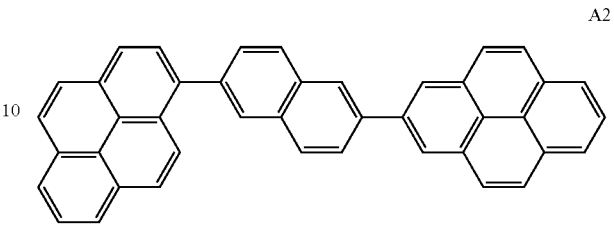

A2

The HOMO level of the compound A2 was −8.06 eV.

[Chem. 5]

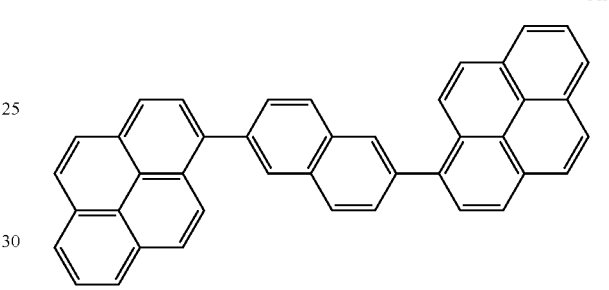

A3

The HOMO level of the compound A3 was −8.13 eV.

The results show that the HOMO level of the compound A2 is shallower than that of the compound A3. This is because the 2-pyrenyl group illustrated on the right side of the structural formula has a greater electron-donating property than the 1-pyrenyl group.

Examples of the pyrene compound of the present invention are as follows.

[Chem. 6]

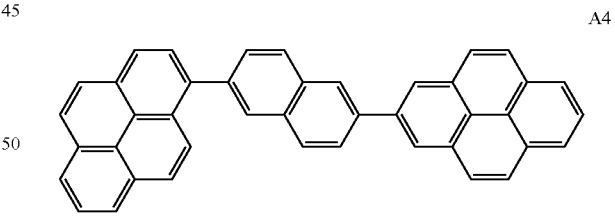

A4

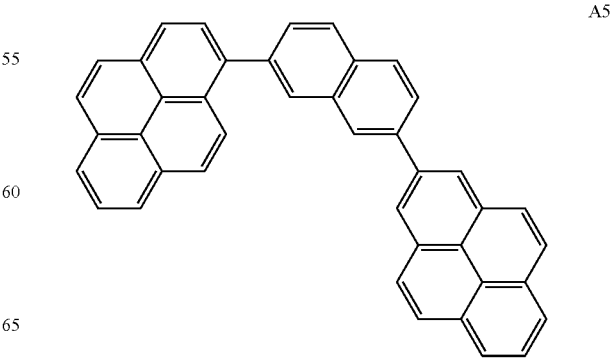

A5

A6
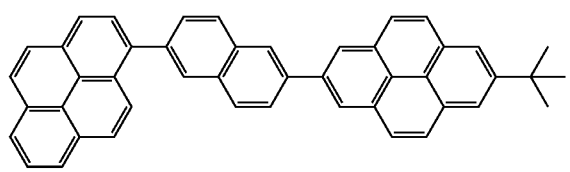
A7
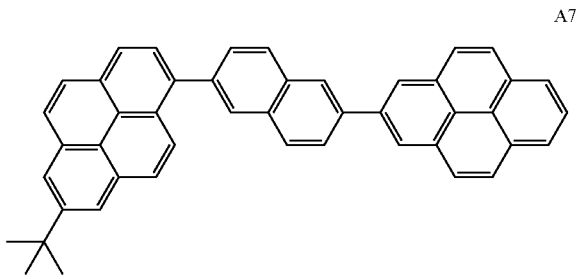
A8
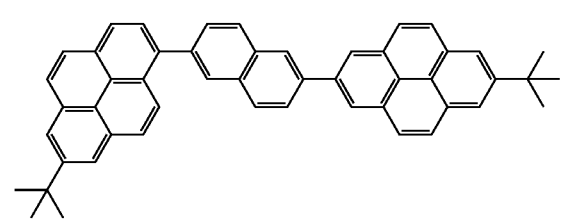
[Chem. 7]
A9
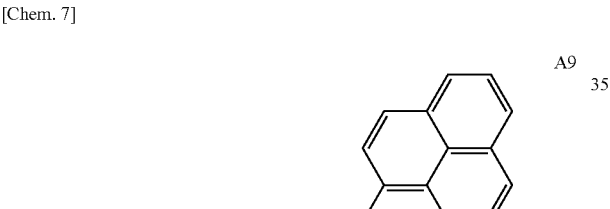
A10
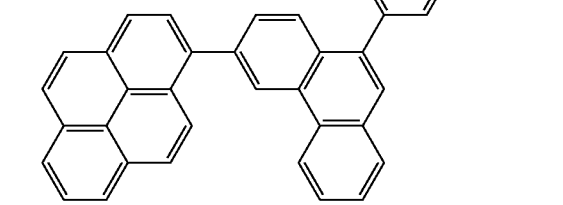
A11
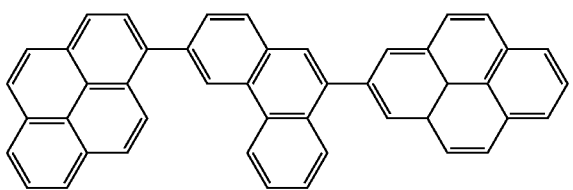
A12
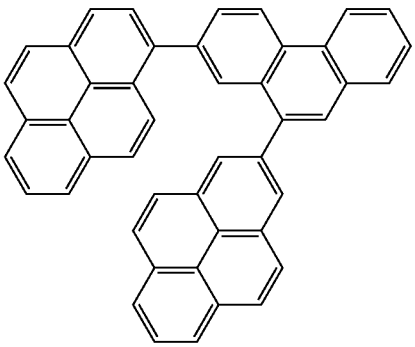
A13
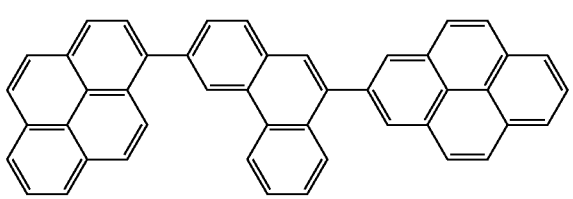
[Chem. 8]
A14
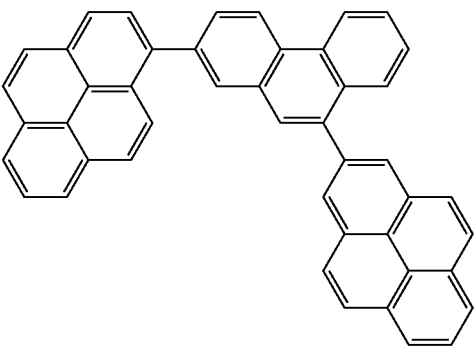
A15

A16

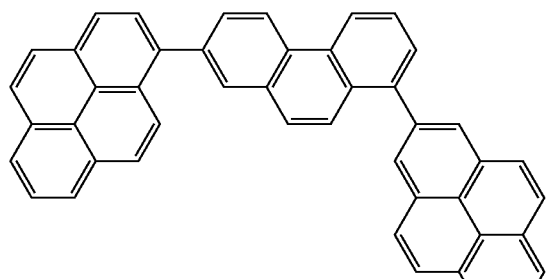

A17

A18

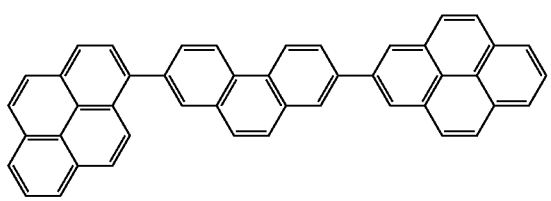

Some of these example compounds are represented by general formulae (2) and (3) below. Compounds represented by general formulae (2) and (3) have high molecular stability. This is because in the compounds represented by general formulae (2) and (3), the dihedral angle formed by the naphthalene or phenanthrene ring and the 1-pyrenyl group is small.

[Chem. 9]

General formula (2)

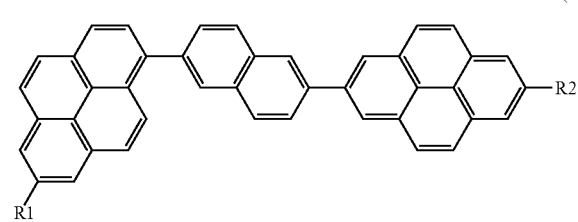

[Chem. 10]

General formula (3)

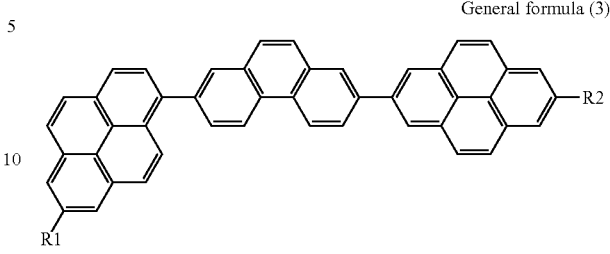

R1 and R2 in general formulae (2) and (3) are each independently selected from a hydrogen group and an alkyl group, as with R1 and R2 of general formula (1).

The process of preparing a pyrene compound represented by general formula (1) is not particularly limited. For example, the pyrene compound can be prepared by the following scheme.

[Chem.11]

Intermediate A

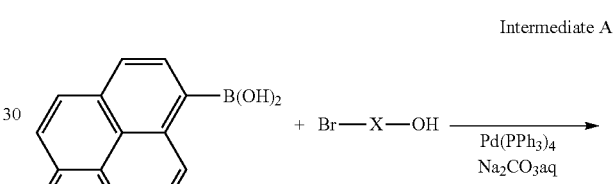

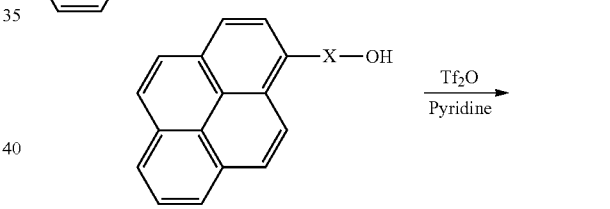

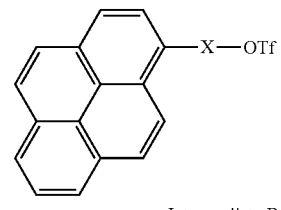

Intermediate B

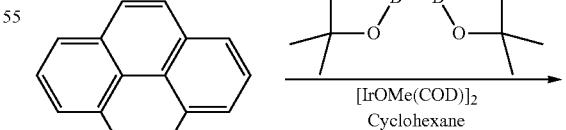

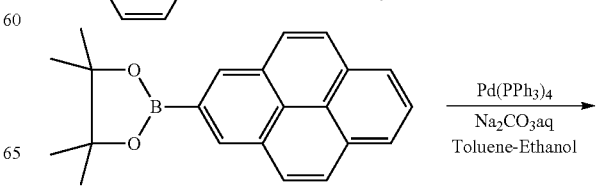

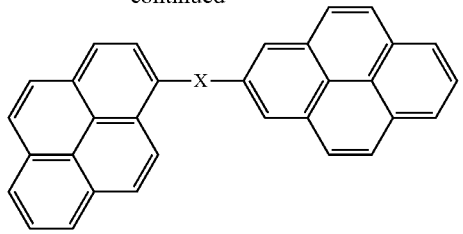

Intermediate A + Intermediate B

Next, an organic EL device containing an organic pyrene compound according to aspects of the present invention is described in detail. The organic EL device according to aspects of the present invention includes an anode, a cathode, an emission layer disposed between the anode and the cathode, and a hole transport layer disposed between the emission layer and the anode. The hole transport layer is in contact with the emission layer. The emission layer of the organic EL device emits light when an electric field is applied between the anode and the cathode.

The emission layer contains a host material and a guest material.

The host material is a pyrene compound represented by general formula (1).

The pyrene compound may be used as a host material of a blue light-emitting layer of an organic EL device.

The pyrene compound has a shallow HOMO level. When the host material in the emission layer of the organic EL device is this compound, the lifetime of the device can be extended. This is because when a compound having a shallow HOMO level is used as the host material, the driving voltage can be lowered and the load imposed on the device is decreased. The pyrene compound is a compound that does not contain any heteroatom. Since a molecule that does not contain any heteroatom is stable against oxidation, the lifetime of the device is extended.

The maximum emission wavelength of the EL emission of a blue light-emitting material is 440 nm or more and 470 nm or less. The band gap is 2.6 eV or more and 2.8 eV or less. In contrast, the band gap of the host material of a blue emission layer may be about 3.0 eV, which is larger than that of the emission material.

The molecule of the pyrene compound described above has a band gap of about 3.0 eV. Accordingly, the pyrene compound according to aspects of the present invention may be used as a host material of an emission layer that contains the host material and the guest material. In particular, the pyrene compound may be used as a host material of a blue emission layer. Alternatively, the pyrene compound may be used as a host material of a green emission layer or as the host material of a red emission layer with a fluorescent material serving as a guest material.

The host material is an organic compound that accounts for the largest weight ratio in the emission layer. The guest material is an organic compound other than the host material in the emission layer.

Examples of the organic EL device including the pyrene compound according to aspects of the present invention are as follows.

An organic EL device according to an embodiment of the present invention may include, in addition to a pair of electrodes, e.g., the anode and the cathode, and the emission layer, a hole transport layer and/or a hole injection layer between the anode and the emission layer, or an electron transport layer, an electron injection layer, and/or a hole-exciton-blocking layer between the emission layer and the cathode, for example. The configuration of the organic compound layers of the light-emitting device containing the compound according to aspects of the present invention is not limited to this.

A material having a large work function is used in the anode. Examples of the material include, but are not limited to, single metals such as Au, Pt, Ag, Du, Ni, Pd, Co, Se, Cr, Mn, V, and W, alloys thereof, and metal oxides such as ITO and IZO. Electrically conductive polymers such as polyaniline, polypyrrole, etc., can also be used. The anode may have a single layer structure or a multilayer structure.

A material having a high hole mobility is used in the hole injection layer and the hole transport layer. An example of such a material is triarylamines but the material is not limited to triarylamines. Triarylamines may be used since the energy barrier between them and the pyrene compound according to aspects of the present invention is low.

A material having a band gap corresponding to blue may be used as the guest material of the emission layer. Examples of such a material include, but are not limited to, chrysene diamine, chrysene diarylamine, and benzofluoranthene.

A material having high electron transport and injection properties may be used in the electron transport layer and the electron injection layer. Examples of such a material include, but are not limited to, triazole derivatives, triazine derivatives, quinoline derivatives, quinoxaline derivatives, phenanthroline derivatives, and organic aluminum complexes.

A material having a small work function is used in the cathode. Examples of such a material include, but are not limited to, single metals such as alkali metals, alkaline earth metals, Al, Ti, Mn, and Ag, alloys thereof, and metal oxides such as ITO. The cathode may have a single layer structure or a multilayer structure.

The organic EL device of this embodiment can be used in display apparatuses and lighting apparatuses. It can also be used as an exposure light source of an electrophotographic image forming apparatus or a backlight of a liquid crystal display apparatus.

A display apparatus includes the organic EL device of this embodiment in a display unit. The display unit includes a plurality of pixels. Each pixel includes the organic EL device of this embodiment and a TFT device. The anode or the cathode of the organic EL device is connected to the drain electrode or the source electrode of the TFT device. The display apparatus can also be used as an image display apparatus of a personal computer or the like.

The display apparatus may be used in a display unit of an imaging apparatus such as a digital camera and a digital video camera. An imaging apparatus includes a display unit and an imaging unit that includes an imaging optical system such as lens and the like. The display apparatus can be used not only in the display unit of an imaging apparatus but also in a display unit of an ink jet printer.

The display apparatus may include an image input unit that inputs information from area CCDs, linear CCDs, and memory cards, for example. The display apparatus may function as a display unit of an imaging apparatus or an ink jet printer and may have both an image output function for displaying images on the basis of image information input from an external device and an input function of inputting processing information on images thereby serving as an operation panel. The display apparatus may be used in a display unit of a multifunctional printer.

Next, a display apparatus that uses the organic EL device according to aspects of the present invention is described.

FIG. 1 is a schematic cross-sectional view showing an organic EL device according to an aspect of the present invention and a thin film transistor (TFT) device, which is an example of a switching device connected to the organic EL device. In the drawing, two pairs of the organic EL device and the TFT device are illustrated. The detailed structures thereof are as follows.

The display apparatus shown in FIG. 1 includes a substrate 1 such as a glass substrate and a moisture-proof film 2 on the substrate 11. The moisture-proof film 12 protects a TFT or organic compound layers. A gate electrode 3 composed of metal is formed on the moisture-proof film 2. A gate insulating film 4 covers the gate electrode 3 and a semiconductor layer 5 covers the gate insulating film 4.

A TFT element 8 includes a semiconductor layer 5, a drain electrode 6, and a source electrode 7. An insulating film 9 is provided on the top of the TFT element 8. An anode 11 of the organic EL device is connected to the source electrode 7 through a contact hole 10. The structure of the display apparatus is not limited to this. For example, one of the anode and the cathode may be connected to one of the source electrode and the drain electrode of the TFT device.

In the drawing, an organic compound layer 12 having a multilayer structure is illustrated as one layer. In order to suppress deterioration of the organic EL device, a first protective layer 14 and a second protective layer 15 are formed on a cathode 13.

The display apparatus including the organic EL device can stably display high quality images over a long time.

EXAMPLES

The present invention will now be described using examples. However, the present invention is not limited to these examples.

Example 1

In order to synthesize compound A8, its intermediates, i.e., A19 and A20, were synthesized as follows. Compound A19 (intermediate B) and compound A20 (intermediate A) were then coupled.

[Chem.12]

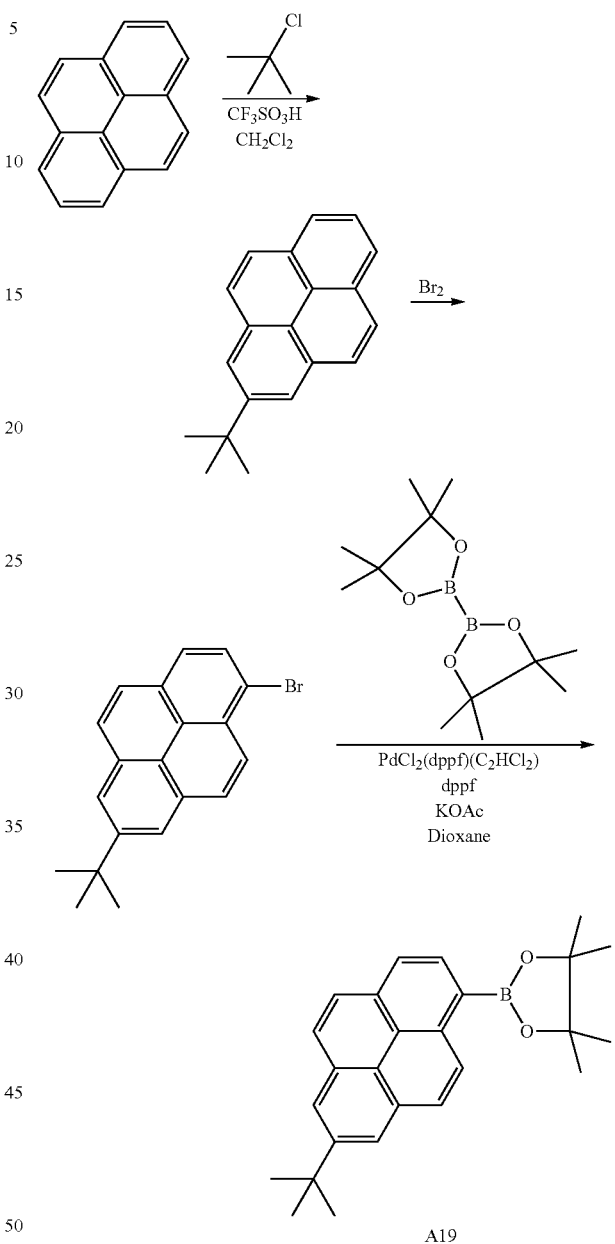

[Chem.13]

-continued

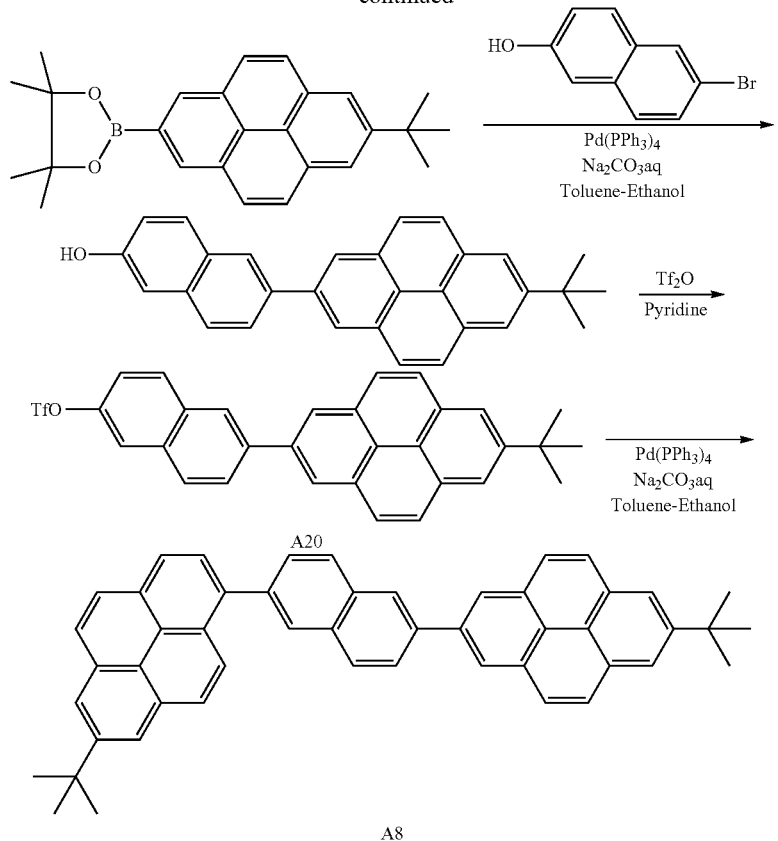

A19 (Intermediate B) + A20 (Intermediate A)

Into a reactor, 80 mL toluene, 40 mL ethanol, 40 mL 10 wt % aqueous sodium carbonate solution, 63.5 mg tetrakis(triphenylphosphine)palladium, 858.3 mg A19, and 1.15 g A20 were charged to obtain a mixture. The reactor was deaerated for several minutes with argon gas to remove oxygen remaining in the system. The reaction mixture was refluxed for 23 hours. After being cooled to room temperature, the mixture was extracted with chloroform. After separation, the organic layer was dried over anhydrous magnesium sulfate and the dehydrate was removed by filtration. The crude product obtained by condensation was recrystallized with chlorobenzene twice and dispersed in acetone to wash. As a result, 1.02 g of A8 was obtained. A8 was identified by $^1$H-NMR and matrix-assisted laser desorption ionization-time of flight (MALDI-TOF) mass spectroscopy.

A chloroform solution of A8 having a concentration of about 0.05 wt % was spin-coated on a glass substrate and the ionization potential (AC-2 produced by RIKEN KEIKI Co. Ltd.) and absorption spectrum were measured. The ionization potential was 5.62 eV and the band gap calculated from the absorption edge of the absorption spectrum was 3.03 eV.

$^1$H-NMR (CDCl$_3$, 400 MHz)

delta=1.60 ppm (s, 9H), 1.62 ppm (s, 9H), 7.87 ppm (dd, 2H), 8.03-8.27 ppm (m, 18H), 8.47 ppm (s, 1H), 8.57 (s, 2H)

MALDI-TOF m/z=639.97 (calc. m/z=640.31)

Compounds A4 to A7, and A9 to A18 were synthesized as with A8 by changing intermediates. Some of them are shown in Table 1 below.

TABLE 1

| Synthesized product | Intermediate A | Intermediate B |
|---|---|---|
| A4 | (pyrene-naphthalene-OTf structure) | (pinacol boronate-pyrene structure) |

TABLE 1-continued

| Synthesized product | Intermediate A | Intermediate B |
|---|---|---|
| A5 | | |
| A6 | | |
| A7 | | |
| A10 | | |
| A17 | | |

Example 2

An organic EL device that includes an anode, a hole injection layer, a hole transport layer, an emission layer, an electron transport layer, and a cathode sequentially layered on a substrate in that order was prepared as below as an example of the structure of an organic EL device.

A glass substrate was used as the substrate. A film composed of indium tin oxide (ITO) having a thickness of 120 nm was sputter-deposited on the glass substrate to form an anode. The ITO film was ultrasonically washed with acetone and then isopropyl alcohol (IPA), boil-washed with IPA, and dried. The substrate and the anode were subsequently washed with UV/ozone so that the substrate could be used as a transparent conductive supporting substrate. A21 represented by the structural formula below was vacuum vapor-deposited on the anode to form a hole injection layer. The thickness of the hole injection layer formed was 40 nm.

[Chem. 14]

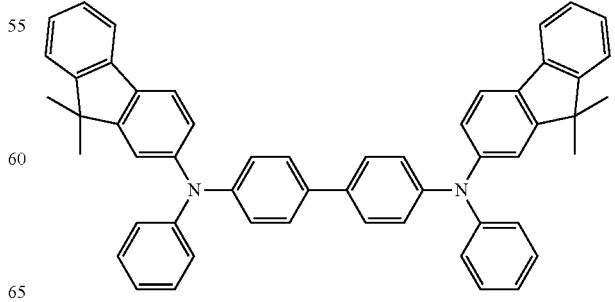

A21

A22 represented by the structural formula below was vacuum vapor-deposited on the hole injection layer to form a hole transport layer. The thickness of the hole transport layer formed was 10 nm.

[Chem. 15]

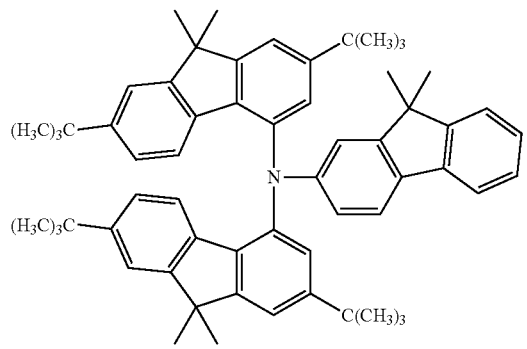

A22

Next, A23 having the structure below and A8 described above were co-deposited at a weight ratio A23:A8=5:95 in vacuum to form an emission layer having a thickness of 30 nm on the hole transport layer.

[Chem. 16]

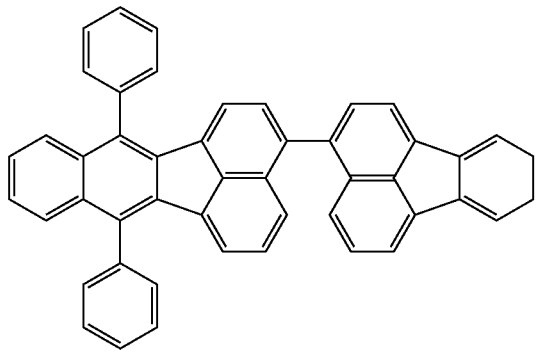 [SMILES: C1=C2C(=CCC1)c1ccc(-c3ccc4c5c(cccc35)-c3c-4c(-c4ccccc4)c4ccccc4c3-c3ccccc3)c3cccc2c13]

A23

2,9-[2-(9,9'-Dimethylfluorenyl]-1,10-phenanthroline was vacuum vapor-deposited on the emission layer to form an electron transport layer having a thickness of 30 nm.

Next, lithium fluoride (LiF) was vacuum vapor-deposited on the electron transport layer to form a film having a thickness of 0.5 nm and an aluminum film having a thickness of 150 nm was vacuum vapor-deposited to form a cathode.

The obtained organic EL device was covered with a protective glass plate in a dry air atmosphere to prevent deterioration caused by moisture adsorption and sealed with an acrylic resin adhesive.

The performance of the device obtained as such was evaluated by connecting an anode to the ITO electrode (anode) and a cathode to the Al electrode (cathode). Emission was measured with BM7 fast produced by TOPCON CORPORATION. A current density of 3.9 mA/cm$^2$ was obtained at 4 V and light with an emission wavelength of 460 nm and an luminous efficacy of 5.8 μm/W was observed. This organic EL device was continuously driven at a current density of 100 mA/cm$^2$. The luminance half life of the device was 1,000 hours.

Comparative Example 1

A25 having the structure below was separately synthesized as a comparative example. The ionization potential and the absorption spectrum were measured as in Example 1. The ionization potential was 5.72 eV and the band gap calculated from the absorption edge of the absorption spectrum was 3.02 eV. Compared to A8 in Example 1, the band gap was substantially the same but the ionization potential was deeper by 0.1 eV, which shows low hole injectability.

[Chem. 17]

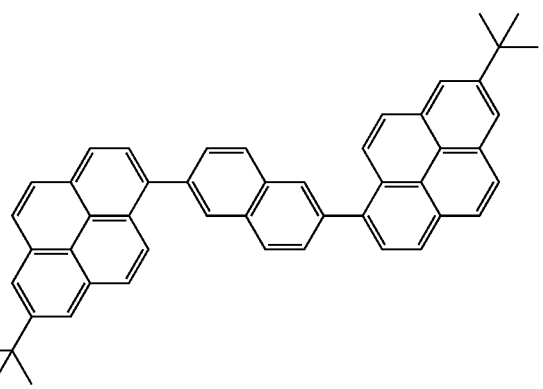

A25

Comparative Example 2

An organic EL device was fabricated as in Example 2 except that A8 was replaced with A25 described in Comparative Example 1. The performance was evaluated as in Example 2. This organic EL device was continuously driven at a current density of 100 mA/cm$^2$. The luminance half life of the device was 500 hours.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-211977, filed Sep. 14, 2009, which is hereby incorporated by reference herein in its entirety.

The invention claimed is:
1. A pyrene compound represented by general formula (1):

General formula (1)

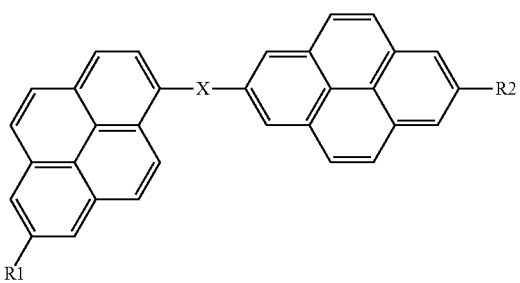

wherein X represents one of a naphthalene ring and a phenanthrene ring; when X represents the naphthalene ring, a 1-pyrenyl group indicated in general formula (1) is bonded to a 2-position of the naphthalene ring; when X represents the phenanthrene ring, the 1-pyrenyl group is bonded to one of a 2-position and a 3-position of the phenanthrene ring; and R1 and R2 are each independently selected from a hydrogen atom and an alkyl group.

2. The pyrene compound according to claim 1, wherein at least one of R1 and R2 represents a tert-butyl group.

3. A host material contained in an emission layer of an organic electroluminescent device, the host material comprising:
the pyrene compound according to claim 1.

4. An organic electroluminescent device comprising:
an anode;
a cathode;
an emission layer interposed between the anode and the cathode; and
a hole transport layer interposed between the emission layer and the anode and in contact with the emission layer,
wherein the emission layer emits light when an electric field is applied between the anode and the cathode,
the emission layer contains a host material and a guest material, and
the host material is the pyrene compound according to claim 1.

5. The organic electroluminescent device according to claim 4, wherein the guest material is a blue light-emitting material.

6. An image display apparatus comprising:
a plurality of pixels each including the organic electroluminescent device according to claim 4 and a thin film transistor device,
wherein the anode or the cathode of the organic electroluminescent device is connected to a drain electrode or a source electrode of the thin film transistor device.

7. An image input apparatus comprising:
a display unit; and
an image input unit configured to read images,
wherein the display unit includes a plurality of pixels each including the organic electroluminescent device according to claim 4 and a thin film transistor device, and the anode or the cathode of the organic electroluminescent device is connected to a drain electrode or a source electrode of the thin film transistor device.

8. An organic electroluminescent device comprising:
an anode;
a cathode; and
an emission layer interposed between the anode and the cathode, the emission layer comprising the pyrene compound according to claim 1.

9. The organic electroluminescent device according to claim 8,
wherein the emission layer comprises a host and a guest, and
wherein the host is the pyrene compound.

10. The organic electroluminescent device according to claim 9,
the guest is a compound represented by the following structure 11. A lighting apparatus comprising the organic electroluminescent device according to claim 8.

12. An electrophotographic image forming apparatus comprising an exposure light source,
the exposure light source comprising the organic electroluminescent device according to claim 8.

13. An exposure light source of an electrophotographic image forming apparatus comprising the organic electroluminescent device according to claim 8.

* * * * *